United States Patent
Johnson

(10) Patent No.: US 12,048,598 B1
(45) Date of Patent: Jul. 30, 2024

(54) SYSTEM AND METHOD FOR HEAD AND NECK SUPPORT DEVICE

(71) Applicant: Bradley Curtis Johnson, Pasadena, CA (US)

(72) Inventor: Bradley Curtis Johnson, Pasadena, CA (US)

( * ) Notice: Subject to any disclaimer, the term of this patent is extended or adjusted under 35 U.S.C. 154(b) by 262 days.

(21) Appl. No.: 17/585,490

(22) Filed: Jan. 26, 2022

Related U.S. Application Data

(60) Provisional application No. 63/141,943, filed on Jan. 26, 2021.

(51) Int. Cl.
*A61B 90/60* (2016.01)

(52) U.S. Cl.
CPC .................................... *A61B 90/60* (2016.02)

(58) Field of Classification Search
CPC ........................................................ A61B 90/60
See application file for complete search history.

(56) References Cited

U.S. PATENT DOCUMENTS

| | | | | |
|---|---|---|---|---|
| 1,409,326 A * | 3/1922 | Williamson | ............... | A61F 5/02 2/44 |
| 4,383,523 A | 5/1983 | Schurman | | |
| 4,934,354 A | 6/1990 | Anapliotis | | |
| 5,199,940 A * | 4/1993 | Morris | .................... | A61F 5/055 602/17 |
| 5,242,377 A | 9/1993 | Boughner et al. | | |
| 5,248,293 A * | 9/1993 | Hubbard | ................. | A61F 5/055 602/17 |
| 5,832,926 A | 11/1998 | Towlen | | |
| 6,931,669 B2 * | 8/2005 | Ashline | ................. | B60R 22/001 280/801.1 |
| 6,971,123 B2 * | 12/2005 | Weaver | .............. | A63B 71/1291 2/468 |
| 8,834,394 B2 * | 9/2014 | Ghajar | .................... | A61F 5/055 602/17 |
| 11,382,378 B2 * | 7/2022 | Margetis | ............. | A42B 3/0473 |

(Continued)

FOREIGN PATENT DOCUMENTS

| CN | 104983544 | 10/2017 |
|---|---|---|
| CN | 108309538 | 7/2018 |

(Continued)

OTHER PUBLICATIONS

Headactive Technical Data and Instructions of Use Source: https://www.medicaleshop.com/pdfs/pacific-rehab/headpod/head-active-user-manual.pdf Date Accessed: Jun. 24, 2020.

(Continued)

*Primary Examiner* — Monica E Millner
(74) *Attorney, Agent, or Firm* — Michelle L. Gross, P.C.

(57) ABSTRACT

A system and method for reducing fatigue, preventing fatigue, or generally supporting a user's head and neck during extended periods of looking downward without restricting a user's range of motion by a user-wearable neck and head support device comprising an adaptable vest optionally configured with straps, back plates, support structures, a customizable bracing rod optionally configured with anchor plates and brackets, an adjustable headpiece with optionally configured accessories, and a wire slidably and detachably coupled to a rail on the headpiece that may be optionally configured with a wire tension controller and a quick release connector.

20 Claims, 6 Drawing Sheets

(56) References Cited

U.S. PATENT DOCUMENTS

| | | | |
|---|---|---|---|
| 2005/0245854 A1* | 11/2005 | Leuthardt | A61F 5/026 602/18 |
| 2010/0204628 A1 | 8/2010 | Ghajar | |
| 2010/0286581 A1* | 11/2010 | Hipp | A61F 5/055 602/18 |
| 2012/0136292 A1 | 5/2012 | Pepin | |
| 2013/0261520 A1 | 10/2013 | Grenander | |
| 2015/0202072 A1 | 7/2015 | Glazener et al. | |
| 2020/0245708 A1* | 8/2020 | Margetis | A42B 3/0473 |
| 2020/0390517 A1* | 12/2020 | Zeilah | A61B 90/60 |
| 2022/0257336 A1* | 8/2022 | Malcolm | A61B 90/53 |

FOREIGN PATENT DOCUMENTS

| | | |
|---|---|---|
| CN | 208756277 | 4/2019 |
| DE | 202019102151 | 6/2019 |
| WO | 2013003369 | 1/2013 |

OTHER PUBLICATIONS

Adjustable Neck Chest Cervical Thoracic Head Back Brace Orthosis Corrector T Source: https://www.ebay.com/itm/Adjustable-Neck-Chest-Cervical-Thoracic-Head-Back-Brace-Orthosis-Corrector-Tools-/264438687668?_trksid=p2385738.m4383.110137.c10&nordt=true&rt=nc&orig_cvip=true Date Accessed: Jun. 24, 2020.

* cited by examiner

Securing a vest around a portion of a torso of a user.
[610]

Securing a headpiece around at least a portion of the user's head.
[620]

Adjusting a tension of a wire coupled to a bracing rod coupled to a rear of the vest to apply a force pulling away from a posterior of the user's head where the wire is further slidably and detachably coupled to a rail coupled to the headpiece. [630]

SYSTEM AND METHOD FOR HEAD AND NECK SUPPORT DEVICE

CROSS REFERENCE TO RELATED APPLICATIONS

This application claims the benefit of priority to U.S. Provisional Application No. 63/141,943, filed on Jan. 26, 2021, the entirety of this application is hereby incorporated herein by reference.

BACKGROUND

1. Field of the Invention

The field of the present invention generally relates to exemplary embodiments of a head and neck support device configured to support the user's head and neck during extended periods of looking downward. This invention also generally relates to exemplary embodiments of a head and neck support device while in use.

2. Description of Related Art

Surgeons, specifically orthopedic surgeons, often must look in a downward direction for extended periods of time during surgical procedures. This commonly leads to neck fatigue due to the extended duration that the head must be looking downward. While devices exist to support a user's head and neck, these devices have historically been very rigid, constrain, or resist the user's range of motion of the head, some even having been designed to immobilize the user's head and/or neck to allow for rehabilitation after a neck injury.

So as to reduce the complexity and length of the Detailed Specification, and to fully establish the state of the art in certain areas of technology, Applicant(s) herein expressly incorporate(s) by reference all of the following materials identified in each numbered paragraph below.

Chinese Patent CN 208756277 U (Cajun) describes a portable wearable cervical vertebra and lumbar vertebrae protection device, including assistance for arms, designed for keeping the human body, head, and waist standing upright. Cajun's disclosure also describes U-shaped or T-shaped boards and multiple fixed plates.

US Patent US 2013/0261520 A1 (Grenander) describes a neck relief device for sedentary jobs and repetitive static tasks that cause problems particularly of the shoulders and neck. Grendander's disclosure describes a forehead band, a lower fixing device or belt, and an elastic band with ends shaped secured directly between the band and the belt that uses a tensile force so adapted as to exceed the natural forward torque of the head and promote a more upright posture.

US Patent US 2010/0204628 A1 (Ghajar) describes an apparatus and methods for reducing brain and cervical spine injury by preventing the head from substantial rotational acceleration or deceleration that could lead to tearing of brain or cervical spine tissue. Ghajar's disclosure includes a headpiece having a first attachment member; a support harness sufficiently designed to secure to the user's torso, the support harness having a second attachment member; and a telescoping member having a main tube and a series of progressively smaller diameter tubes nested within each other, adapted to extend and compress in a linear plane by the intake and outflow of fluid.

U.S. Pat. No. 5,242,377 A (Boughner) describes a tethered medical restraint device that allows the head to rotate while maintaining the head in a desired secured position by a bending plate with a tensioning means. Boughner's disclosure includes a first plate that extends along the back of the torso and is strapped to the torso by a torso harness, a second plate that extends upward from the first plate behind the head and neck of the person, and a head harness for grasping the head is attached to the device by a tether mounted on the second plate.

US Patent Application US 2005/0245854 A1 (Leuthardt) describes a cervical brace for restraining movement of a head and neck vertebra of a patient. Leuthardt's disclosure includes a mount extending upward from the mount to a position in use, a loop sized and shaped for receiving the head of the patient cantilevered from the support and at least one joint for adjusting at least one of a pitch, a yaw and a roll of the loop relative to the mount.

German Patent DE 202019102151 U1 (Haeussler) describes an orthosis for supporting the head of a patient, in particular an ALS (Amyotrophic Lateral Sclerosis) patient, that has among the many different symptoms, the so-called Dropped Head Syndrome (DHS), that is a very serious symptom in which the patient can not sufficiently support or even lift his head due to severely atrophied neck muscles. Haeussler's disclosure includes a head part, a body attachment and a connection element, where the connection element is arranged between the head part and the body attachment, comprises at least one means for adjusting a force acting between the head part and the body attachment, and minimizes parasitic forces during rotation.

US Patent US 2015/0202072 A1 (Glazener) describes a cervical spine orthosis that include a brace that includes a head frame, a strap assembly and a cervical bar where the cervical bar has a stiffness sufficient to support the head and the head frame against head drop.

Chinese Patent 108309538 A (Bengbu Medical College) describes a medical adjustable torticollis orthosis device that comprises a head assembly, chest fixing device, support bars that include upper and lower jaw supports for a common pediatric disease of skeletal congenital muscular torticollis.

U.S. Pat. No. 5,832,926 A (Towlen) describes a head support device for restraining and supporting the head of a user at a given forward angle while alleviating resultant neck, shoulder, and back pain that comprises an angularly adjustable upper section contacting the head of a user, a fixed intermediate section for transmitting the force applied by the head of a user to the device to the user's upper back and shoulders, and a lower section contacting the lower back of a user. Towlen's disclosure describes a device that is attached to the body of a user by a back support belt.

WIPO (PCT) Patent Application WO 2013/003369 A2 (Sacksteder) describes a human support system that is an adjustable support system provided for holding human arms in fixed or moving positions and providing support for other portions of the body that may be subjected to strain configurable for use in a variety of postures including sitting, standing and crouching. Sacksteder's disclosure included pivoting joints can be compliant within a settable range of motion, and the torsional forces produced at the pivoting joints can be variable by use of an elastic element acting across the fixed and movable sides of the rotary joints.

U.S. Pat. No. 4,383,523 A (Schurman) describes a cervical brace that has an independently adjustable chin support and occipital supports for constraining movement of the head in any direction. Schurman disclosures chin, occipital rests that are connected together by means of rigid lateral slide supports, and front and rear support mechanisms that are held in position on the body by means of a fabric corset.

U.S. Pat. No. 4,934,354 A (Anapliotis) describes a device for externally fixing and/or imparting traction to the cervical spine having a fastening ring attached to the patient's head, a plurality of support bearings affixed to the chest and/or back of the patient and the fastening and support bearing are connected together by plural connecting rods that included clamping elements and ball joints which are connected to the connecting rods by the clamping elements.

Chinese Patent 104983544 B (Harbin) describes a kind of wearable cervical vertebra rehabilitation medical robot. Harbin's disclosure includes an upper headgear and upper body fixed support with a ball pivot and its bearing with actuator, where the actuator can be driven by the various ways such as hydraulic pressure, electronic, pneumatic. Harbin's disclosure describes the robot undertaking the part or all of weight of the brain while not limiting to the motion of the brain.

US Patent Application US 2012/0136292 A1 (Pepin) describes a non-invasive cervical-thoracic correction system for therapeutic use and for correction of abnormalities in a person's posture is disclosed. Pepin's disclosure comprises a chest brace that includes shoulder supports that fit to the person's shoulders; a body harness connected to the chest brace by way of one or more support straps so as to provide a stable foundation when fitted to the person; and a forehead pad mounted to the chest brace by way of a spring connection that includes a helix spring and that provides a variable amount of tension to the forehead pads such that the person's head is biased into a position that is in keeping with normal posture.

Applicant(s) believe(s) that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Applicant(s) will amend the specification to expressly recite the essential material that is incorporated by reference as allowed by the applicable rules.

SUMMARY

The present invention provides among other things a head and neck support device configured to support the user's head and neck during extended periods of looking downward. Implementations of a user-wearable neck and head support device may provide support, such as by reducing or preventing fatigue, of a user's head or neck during extended periods of looking downward without restricting range of motion.

Implementations of a user-wearable neck and head support device may provide for a vest, a bracing rod coupled to a rear of the vest, a headpiece configured to seat around at least a portion of a user's head, the headpiece coupled to the bracing rod and further including a rail, where the rail is positioned proximal a rear of the user's head, and a wire that is coupled to the bracing rod and slidably and detachably coupled to the rail.

Particular aspects of the user-wearable neck and head support device may provide for the vest to include an adjustable strap and a back plate coupled to the adjustable strap. Particular aspects of the user-wearable neck and head support device may provide a for the vest to include a hip strap. Another aspect of the user-wearable neck and head support device may provide the vest to include a bracket coupled to the back plate and the bracing rod.

Particular aspects of the user-wearable neck and head support device may provide for the bracing rod to be comprised of a flexible material. Particular aspects of the user-wearable neck and head support device may provide for an anchor plate to be coupled to the back plate and the bracing rod. Particular aspects of the user-wearable neck and head support device may provide for the bracing rod to be telescopic. Another aspect of the user-wearable neck and head support device may provide for a wire tension controller within the user-wearable neck and head support device or at least one of the vest or the hip strap.

Particular aspects of the user-wearable neck and head support device may provide for a wire quick-release connector within the user-wearable neck and head support device or coupled to the wire. Particular aspects of the user-wearable neck and head support device may provide for a diameter of the headpiece to be adjustable.

Implementations of a user-wearable neck and head support device, may provide a method for supporting a user's head and neck using a user-wearable neck and head support device by securing a vest around a portion of a torso of a user, securing a headpiece around at least a portion of the user's head, and adjusting a tension of a wire coupled to a bracing rod coupled to a rear of the vest to apply a force pulling away from a posterior of the user's head where the wire is further slidably and detachably coupled to a rail coupled to the headpiece.

Particular aspects of the user-wearable neck and head support device may provide for the method supporting a user's head and neck using a user-wearable neck and head support device where the vest further comprises an adjustable strap and a back plate coupled to the adjustable strap. Particular aspects of the user-wearable neck and head support device may provide for the method supporting a user's head and neck using a user-wearable neck and head support device where the vest further includes a hip strap. Another aspect of the user-wearable neck and head support device may provide for the method supporting a user's head and neck using a user-wearable neck and head support device where a bracket is coupled to the back plate and the bracing rod.

Particular aspects of the user-wearable neck and head support device may provide for the method supporting a user's head and neck using a user-wearable neck and head support device where the bracing rod is comprised of a flexible material. Particular aspects of the user-wearable neck and head support device may provide for the method supporting a user's head and neck using a user-wearable neck and head support device where an anchor plate is coupled to the back plate and the bracing rod. Particular aspects of the user-wearable neck and head support device may provide for the method supporting a user's head and neck using a user-wearable neck and head support device where the bracing rod may be telescopic. Another aspect of the user-wearable neck and head support device may provide for the method supporting a user's head and neck using a user-wearable neck and head support device where adjusting the tension of the wire comprises adjusting a wire tension controller within at least one of the vest and the hip strap.

Particular aspects of the user-wearable neck and head support device may provide for the method supporting a user's head and neck using a user-wearable neck and head support device where a wire quick-release connector is coupled to the wire. Particular aspects of the user-wearable neck and head support device may provide for the method supporting a user's head and neck using a user-wearable neck and head support device where a diameter of the headpiece is adjustable.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographers, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of 35 U.S.C. § 112(f). Thus, the use of the words "function," "means" or "step" in the Detailed Description or Description of the Drawings or Claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

The foregoing and other aspects, features, and advantages will be apparent to those artisans of ordinary skill in the art from the DETAILED DESCRIPTION, DRAWINGS, and CLAIMS.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Figure 1:
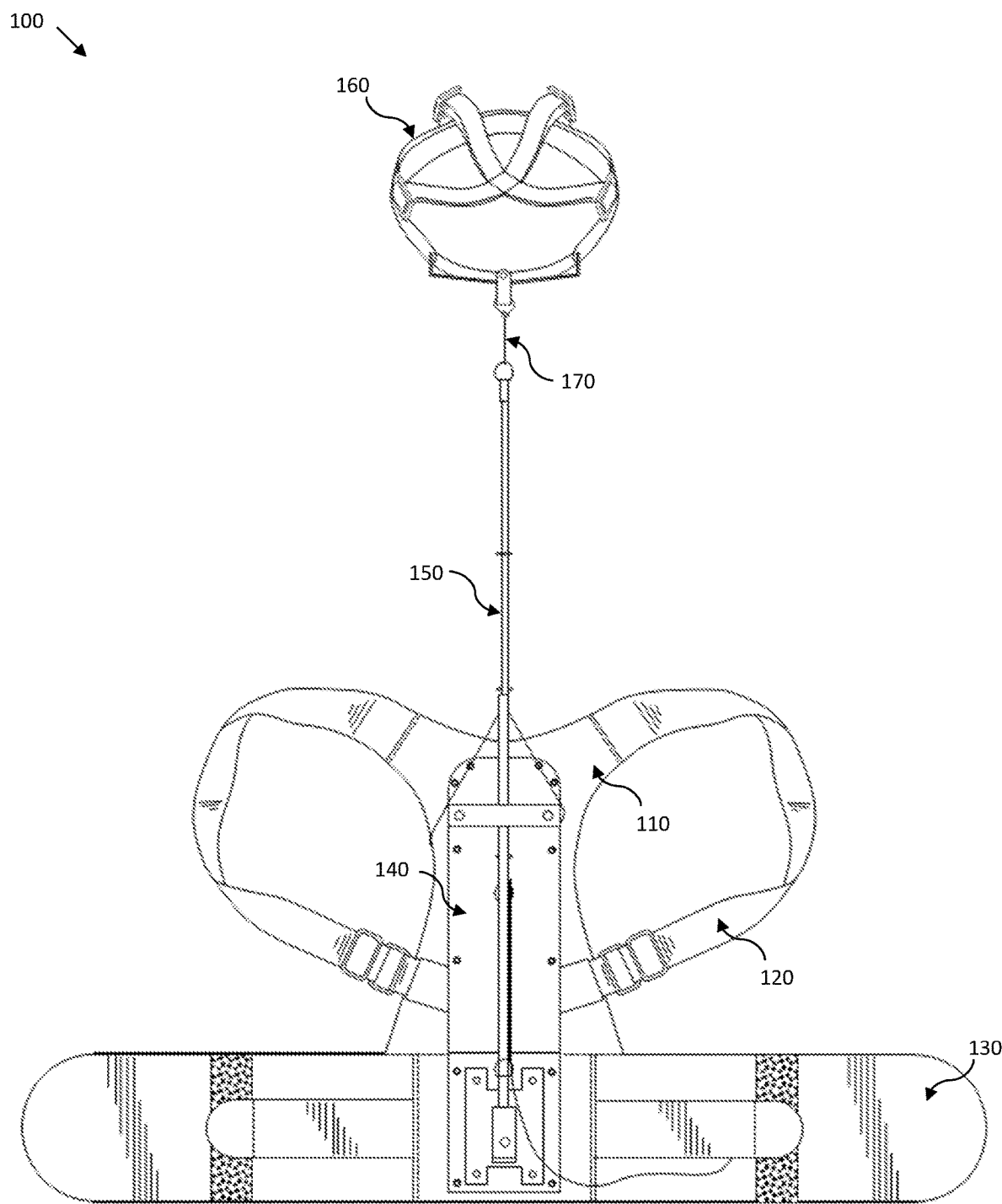
FIG. 1 representatively illustrates a rear perspective view of a non-limiting exemplary implementation of a head and neck support device.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

In one application, a head and neck support device 100 according to various aspects of an embodiment of the invention provides support, such as by reducing or preventing fatigue, of a user's head or neck during extended periods of looking downward without restricting range of motion. In one embodiment, a head and neck support device 100 may comprise a vest 110, a bracing rod 150, a headpiece 160, and a wire 170 as shown in FIG. 1 to FIG. 5. In another embodiment, a head and neck support device 100 may comprise a vest 110, a bracing rod 150, a headpiece 160, a wire 170, and a fastener. In another one embodiment, a head and neck support device 100 may comprise a vest 110, a bracing rod 150, a headpiece 160, a wire 170, and a support structure. In another embodiment, a head and neck support device 100 may comprise a vest 110, a bracing rod 150, a headpiece 160, a wire 170, a fastener, and a support structure. In one embodiment, a head and neck support device 100 may be configured to be flexible. In one embodiment, a head and neck support device 100 may be configured to not restrict the user 210's range of motion of the user's head. In one embodiment, a head and neck support device 100 may be configured to provide unencumbered motion of the user's head, such as by reducing or eliminating drag or friction from components of the neck and back support device 100 during motion of the user's head. The head and neck support device 100, may however, be configured in any suitable matter to interface with the user 210 and to reduce fatigue, prevent fatigue, or generally support the user's head and neck during extended periods of looking downward.

The vest 110, according to various aspects of an embodiment of the invention provides for comfort, stability, customized fit, and security of the neck and head support device 100 on the user 210 as shown in FIG. 1 to FIG. 5. In one embodiment, vest 110, may comprise a strap. In one embodiment, the strap may be configured as an adjustable strap 120 as shown in FIG. 1 to FIG. 5. In another embodiment, the adjustable strap 120 may be configured to be coupled to the back plate 140. In another embodiment, the vest 110 may comprise a plurality of adjustable straps 120 configured to allow the user 210 to customize the fit of the vest for comfort and stability. In one embodiment, the strap may be configured as a hip strap 230 as shown in FIG. 1 to FIG. 5. In one embodiment, the hip strap 230 may be configured to secure around the torso, waist, or hips of the user 210. In another embodiment, the strap may be configured as a torso strap, a waist strap, a shoulder strap, an arm strap, or a leg strap. In one embodiment, a head and neck support device 100 may comprise a plate. In one embodiment, the plate may comprise a back plate 140 as shown in FIG. 1 to FIG. 5. In one embodiment, the vest 110 may be configured as a standalone vest 110 or an integrated vest 110, such as a vest 110 integrated into a piece of clothing or another wearable item. The vest 110, may however, be configured in any suitable matter to provide an interface between the neck and head support and the user 210; customize the fit of and secure the neck and head support device 100 to the user 210 for comfort and stability; and to facilitate, increase, decrease, or maintain the level of support the neck and head support device 100 provides to the head and neck of the user 210.

The bracing rod 150, according to various aspects of an embodiment of the invention allows for the user 210 to move the user's head in a downward direction while still being supported by the head and neck support device 100. In one embodiment, the bracing rod 150 is configured as a flexible material, such as a flexible bracing rod as shown in FIG. 1 to FIG. 5. In one embodiment, the flexible bracing rod may be configured to allow the user 210 to move the user's head in a downward direction while still being supported by the head and neck support device 100. In another embodiment, the bracing rod 150 may be comprised of a material, such as one or more of a wood, a metal, an alloy, or a composite, including but not limited to fiberglass, carbon graphite, and boron graphite. In another embodiment, the bracing rod 150 is configured as a telescoping bracing rod, such as a bracing rod 150 that may comprise one or more telescoping sections to allow the user 210 to adjust the length of the flexible bracing rod to suit the height of the user 210. In one embodiment, the bracing rod 150 may be configured to be coupled to the headpiece 160. In one embodiment, the bracing rod 150 may be configured to be slidably coupled to the rail of the head piece such that the coupling point slides along the rail when the user 210 turns the user's head from side to side allowing the user 210 to have the ease of being able to turn the users' head from side to side independent of motion of the user's body while the user's head and neck are supported. In one embodiment, the bracing rod 150 may be configured to be coupled to the vest 110 and the hip strap 130 by the back plate 140. In one embodiment, a head and neck support device 100 may comprise an anchor plate 220. In one embodiment, the anchor plate 220, may be configured to security couple components of the neck and head support device 100, such as back plate 140 or bracing rod 150 to the vest 110 or hip strap 130 using at least one bracket 230. In one embodiment, the anchor plate 220 may be configured to couple the back plate 140 to the bracing rod 150. In one embodiment, a head and neck support device 100 may comprise a bracket 230. In one embodiment, the bracket 230 may be configured to security couple components of the neck and head support device 100, such as back plate 140 or bracing rod 150 to the vest 110 or hip strap 130 using at least one bracket 230.

In one embodiment, the bracket 230 may be configured to couple the back plate 140 to the bracing rod 150. In one embodiment, the bracing rod 150 may be configured to be securely coupled to the vest 110 or strap using one or more anchor plates 220 or brackets 230 or in conjunction with one or more fasteners, such as a screw, a bolt, a rivet, and the like. The bracing rod 150, may however, be configured in any suitable matter to secure the bracing rod 150 to the vest 110; to facilitate the user's head to bend in a downward direction; and to facilitate, increase, decrease, or maintain the level of support the neck and head support device 100 provides to the head and neck of the user 210.

The headpiece 160, according to various aspects of an embodiment of the invention provides for an interface between the neck and back support device 100 and the user's head. In one embodiment, the headpiece 160 may be configured to seat or to be worn around at least a portion of a head of the user 210 as shown in FIG. 1 to FIG. 5. In one embodiment, the headpiece 160 may be coupled to the bracing rod 150. In one embodiment, the headpiece 160 may comprise a rail 240 as shown in FIG. 1 to FIG. 5. In one embodiment, the headpiece 160 may be configured as standalone headpiece 160 or an integrated headpiece 160, such as a headpiece 160 integrated into a piece of clothing or another wearable item. In one embodiment, the rail 240 may be configured as a track. In another embodiment, the rail 240 may be configured to be positioned proximal to a rear of the user's head. In another embodiment, the rail 240 may be configured to allow for a slidably couple to the bracing rod 150 such that the coupling point slides along the rail 240 when the user 210 turns the user's head from side to side. In another embodiment, the rail 240 may be configured to prevent or minimize drag between the wire and the rail, such as to provide support at all wire contact points along the rail without the user 210 experiencing a substantial change in force as the user 210 turns the user's head from side to side. In one embodiment, the headpiece 160, may be optionally configured with a headpiece accessory. In one embodiment, the headpiece accessory may comprise a light. In another embodiment, the headpiece accessory may comprise a headpiece adjustment knob 260 configured to facilitate adjustment of the headpiece for a user 210, such as adjustment of the diameter of the headpiece 160. The headpiece 160, may however, be configured in any suitable matter to provide an interface between the neck and back support device 100 and the user 210; to allow the user 210 to have the ease of being able to turn the user's head from side to side independent of the motion of the user's body; and to facilitate, increase, decrease, or maintain the level of support the neck and head support device 100 provides to the head and neck of the user 210.

Figure 2:
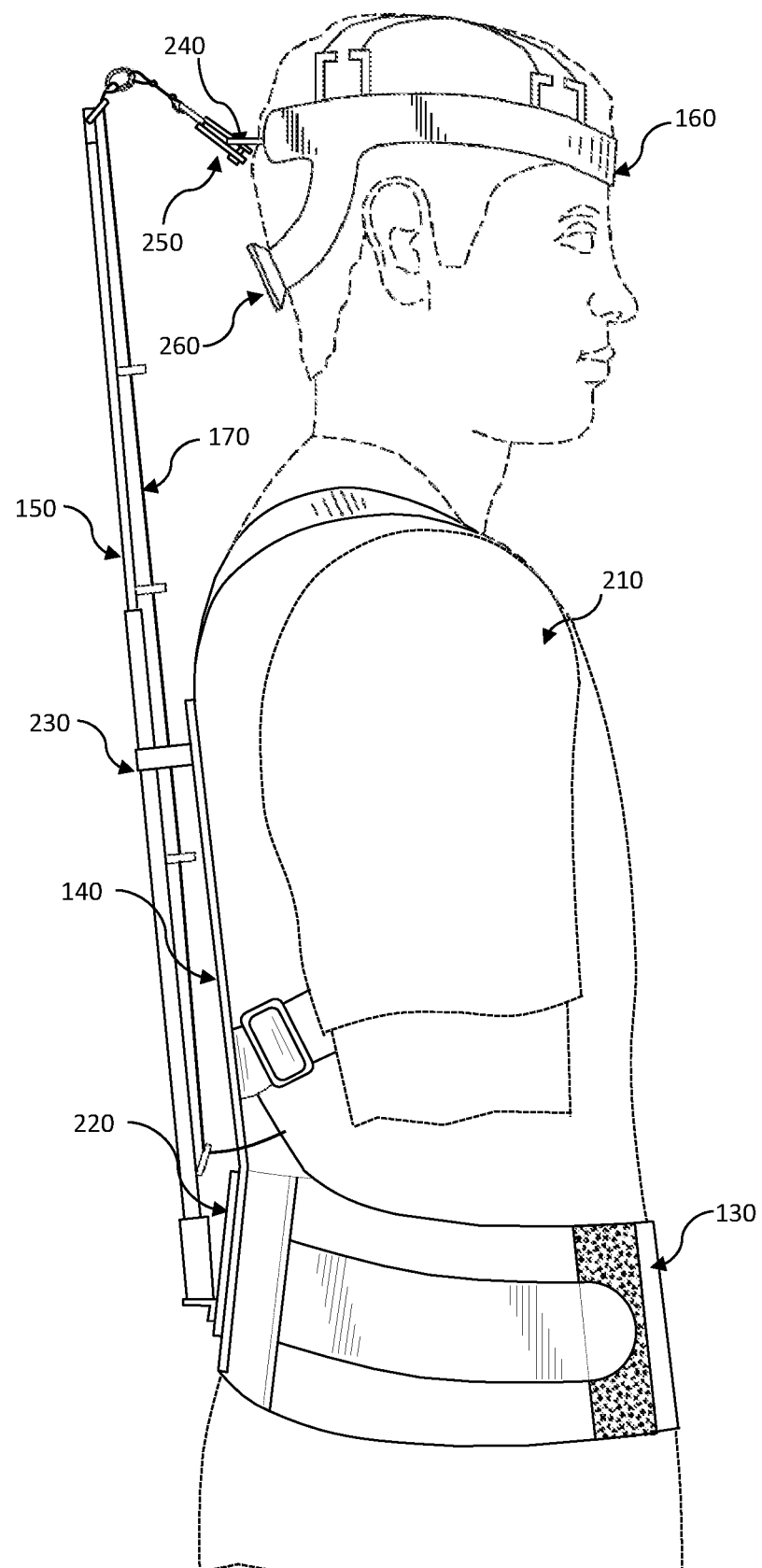
FIGS. 2-3 representatively illustrates side views of the non-limiting exemplary implementation of FIG. 1 when in use.
Figure 3:
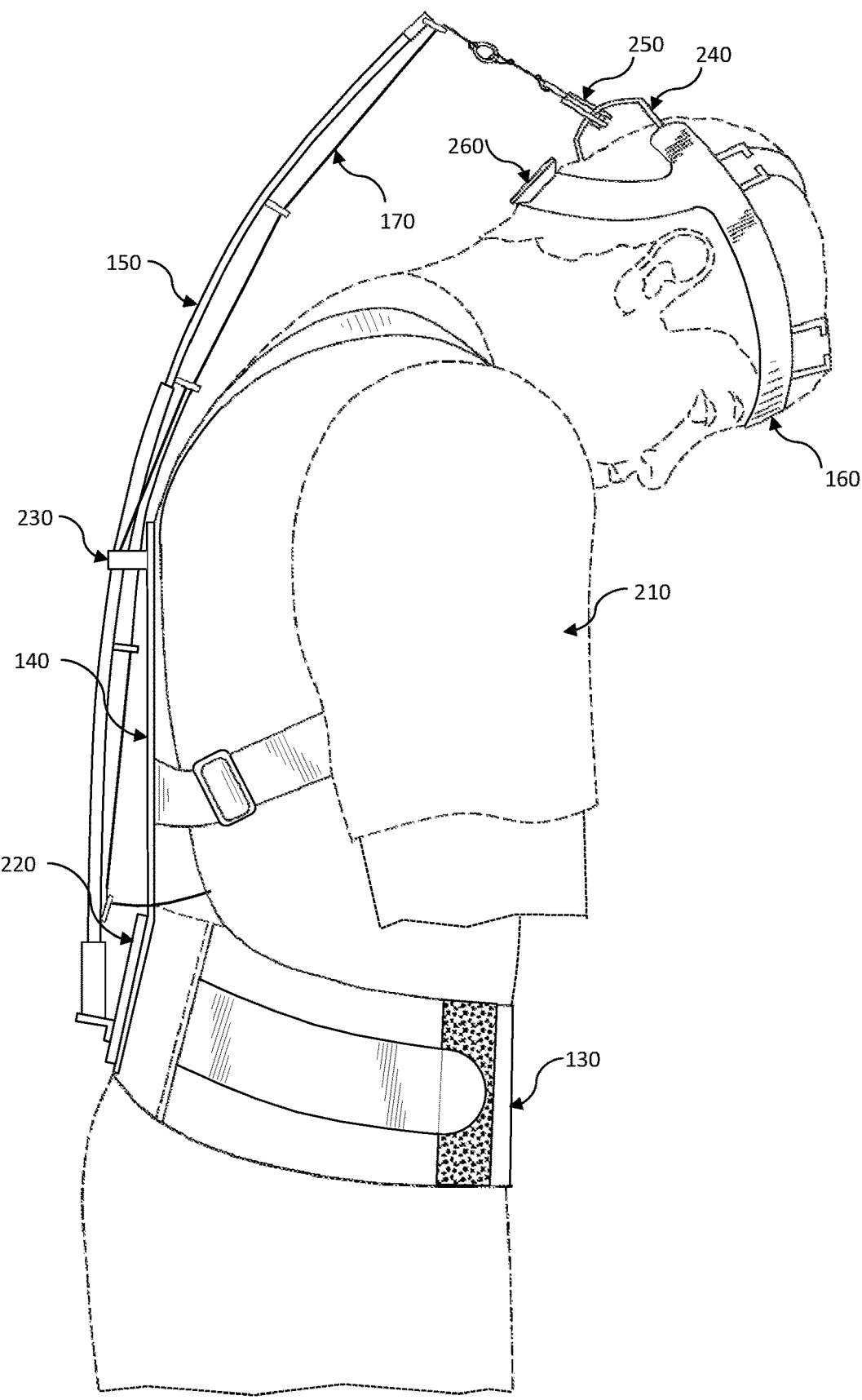
Figure 4:
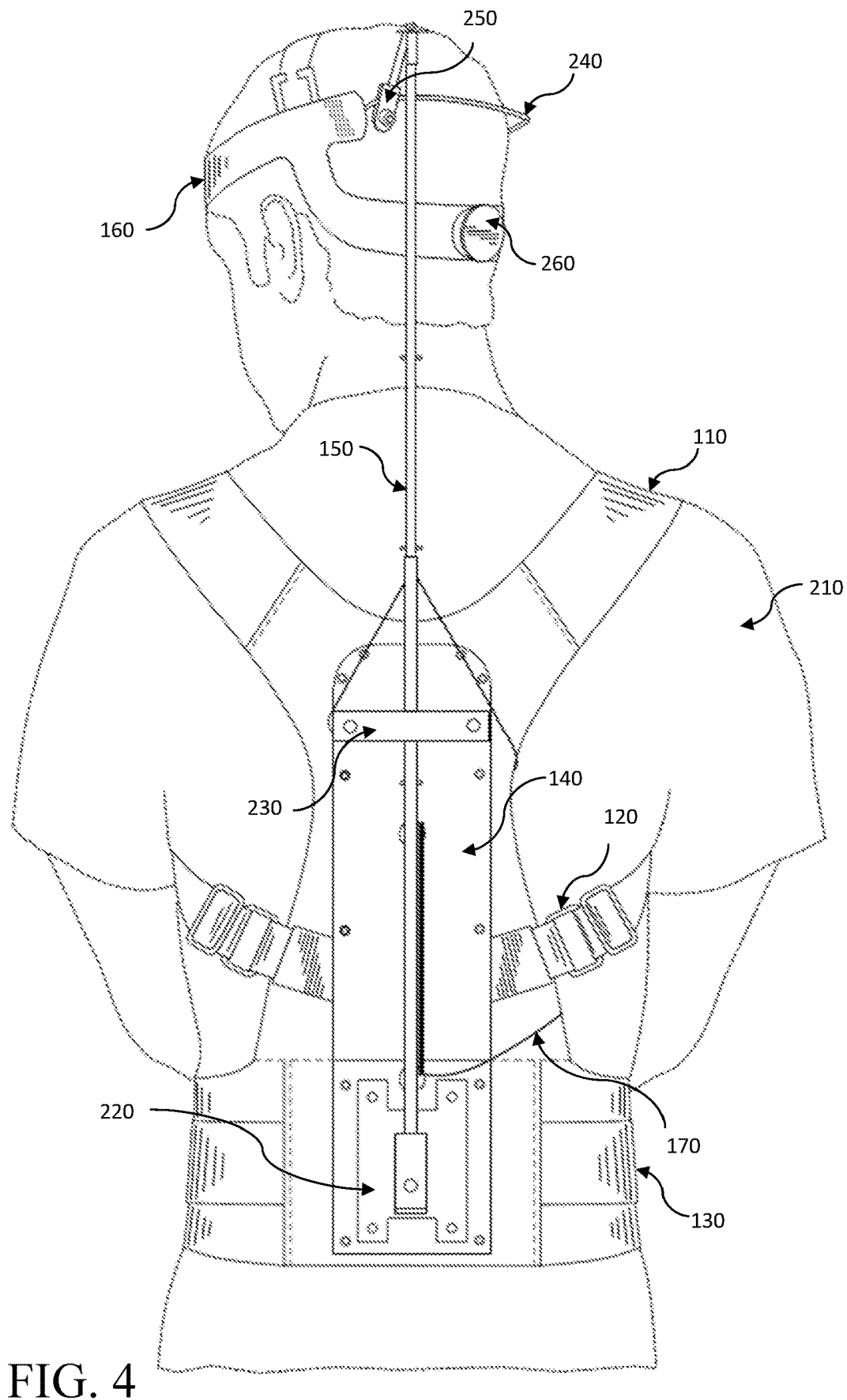
FIGS. 4-5 representatively illustrates rear views of the non-limiting exemplary implementation of FIGS. 1-3 when in use.
Figure 5:
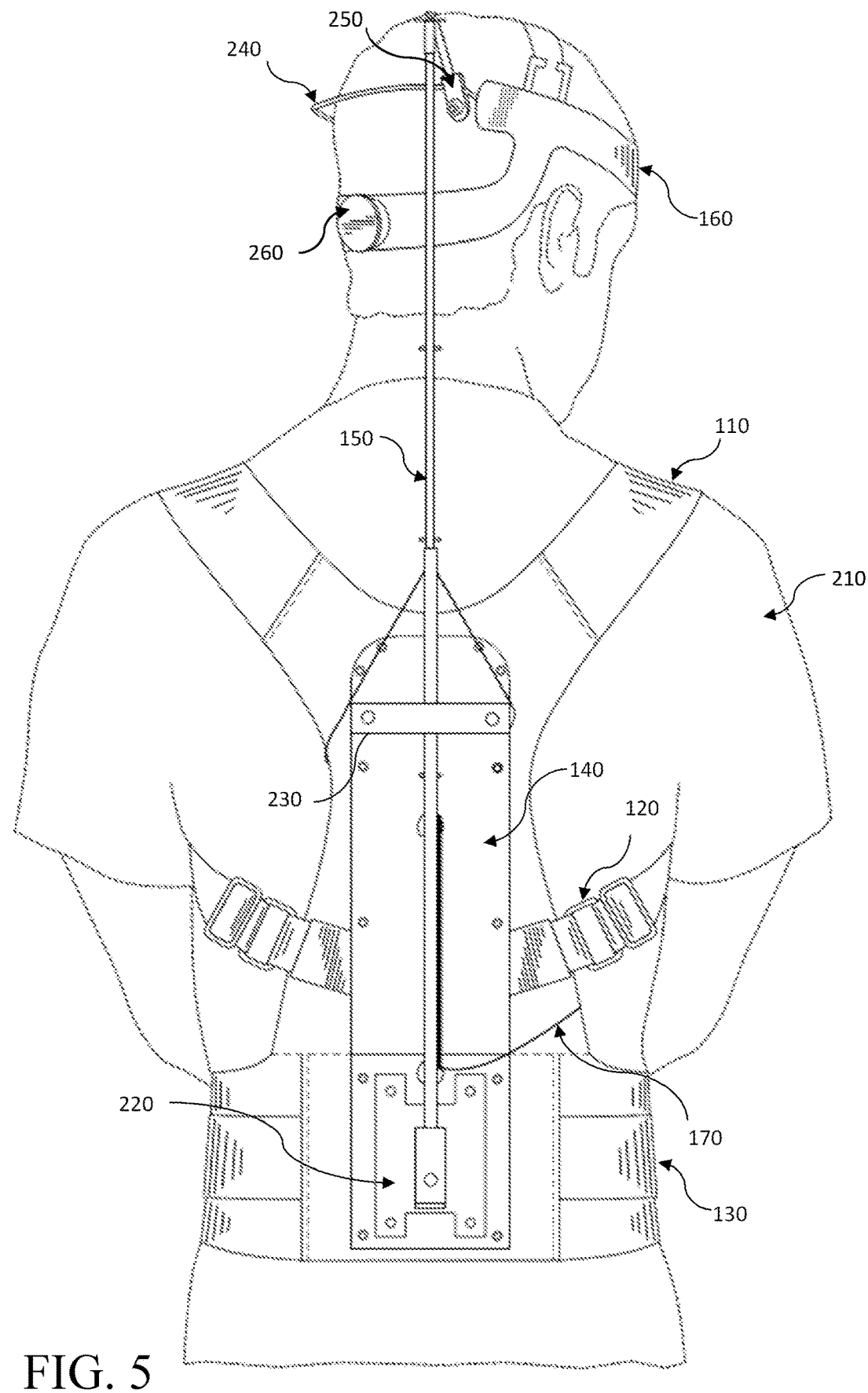

The wire 170, according to various aspects of an embodiment of the invention provides support to the head and neck of the user 210. In one embodiment, the wire 170 may be configured as a cable, a line, or other filament as shown in FIG. 1 to FIG. 5. In another embodiment, the wire 170 may be configured in whole or in part as flexible. In another embodiment, the wire 170 may be configured in whole or in part as not substantially elastic. In another embodiment, the wire 170 may be configured in whole or in part as substantially elastic. In another embodiment, the wire 170 may be configured as a singular filament, a plurality of filaments, or a composite of filaments. In another embodiment, the wire 170 may be configured as a plurality of filaments not coupled to each other, such as running in parallel, or coupled to each other, such as woven or twisted. In another embodiment, the wire 170 may be configured as a filament with additional filament support materials, such as a cross filament support. In one embodiment, the wire 170 may be configured to be coupled to the bracing rod 150 and run longitudinally along at least a portion of the bracing rod 150 as shown in FIG. 2 and FIG. 3. Additionally, in another embodiment while the wire 170, may be configured to run along the bracing rod 150 proximal to the user's body or the wire 170 may run along any side of the bracing rod 150. In another embodiment, the wire 170 may be configured to further extend along or within at least a portion of the vest 110 or hip strap 130 to allow the user 210 to tighten or loosen the tension of the wire 170, such as to allow the user 210 to increase or decrease the level of support of the head and neck of the user 210. In another embodiment, the wire 170 may be configured to allow the user 210 to move the user's head in a downward direction while still being supported by the head and neck support device 100, such as a flexible wire. In one embodiment, the wire 170 may be configured to be coupled to the bracing rod 150 and slidably and detachably coupled to the rail 240. The wire 170, may however, be configured in any suitable matter to interface the vest 110 with the headpiece 160; and to facilitate, increase, decrease, or maintain the level of support the neck and head support device 100 provides to the head and neck of the user 210.

In one embodiment, the fastener may be configured as a screw, a bolt, a nut, a rivet, a weld, an adhesive, or a combination of fasteners. The fastener, may however, be configured in any suitable matter to facilitate securely coupling components of the head and neck support device 100 to other components of the neck and head support device 100 such as the bracing rod 150, the back plate 140, other components of the neck and head support device 100 to the vest 110, the hip strap 130, or a combination of components of the neck and head support device 100 using the anchor plate 220, the bracket 230, or a combination of components of the neck and head support device 100. The fastener, may however, be configured in any suitable matter that when used singularly or in combination provide a flexible, structurally stable, method of securing components of the neck and back support device 100.

In one embodiment, the support structure, may be configured as a supporting strap, a supporting cable, a supporting rod, or other support structure configured to assist in stabilizing components of the neck and head support device 100, such as the back plate 140 or bracing rod 150 relative to the vest 110 or hip strap 130.

In one embodiment, the user 210 may configured as a wearer as shown in FIG. 2 to FIG. 5. In another embodiment, the user 210 may comprise a user's body. In another embodiment, the user 210 may comprise a user's head, user's torso, a user's waist, a user's hips. In another embodiment, the user 210 may configured as a surgeon. In another embodiment, the user 210 may configured as an orthopedic surgeon. Contemplated as part of this disclosure are various embodiments of head and neck support devices 100 and their respective components. It is noted that although this disclosure may refer to head and neck support devices 100 that may be worn by a user 210, such as a surgeon, it is intended that the disclosures described herein may be applied to any of a variety of head and neck support devices 100 used for purposes other than performing surgery, such as riding a bicycle, reading, writing, cooking, performing assembly tasks, operating an electronic device, or operating a remote controlled vehicle, such as a drone. The user 210, may however, be configured in any suitable matter to represent a person requiring support, fatigue reduction, or fatigue prevention of the person's head and neck during extended periods of looking downward without restricting range of motion.

In another application, the head and neck support device 100 may be configured with the bracing rod 150 proximal to the user's body and the wire 170 running along the bracing rod 150 also proximal to the user's body. In another application, the head and neck support device 100 may be configured with the bracing rod 150 that enables the wire 170 to run along any side of the bracing rod 150, such as not being limited to the wire 170 being proximal to the user's body. In another application, the head and neck support device 100 may be configured with the bracing rod 150 proximal to the user's body and a wire 170 distal to the user's body. In another application, the head and neck support device 100 may be configured with the bracing rod 150 distal to the user's body and a wire 170 proximal to the user's body. In another application, the head and neck support device 100 may be configured with the bracing rod 150 and a wire 170 in a similar location, such as side-by-side, to the user's body. In another application, the head and neck support device 100 may be configured with the bracing rod 150 integrated with a wire 170. In another application, the head and neck support device 100 may be configured with the bracing rod 150 designed to contain the wire 170.

In another application, the head and neck support device 100 may be configured with a wire tension controller for adjusting, controlling, or maintaining the amount of support provided by the head and neck support device 100, such as the tension of the wire 170. In one embodiment, the wire tension controller may comprise a spool. In another embodiment, the wire tension controller may comprise a locking mechanism. In one embodiment, the wire tension controller may be coupled to, integrated with, or housed in a component of the neck and back support device 100, such as at least one of the vest 110 and the hip strap 130. In one embodiment, the wire tension controller may be configured to be coupled to or integrated with the bracing rod 150, the headpiece 160, or the wire 170. In one embodiment, the wire tension controller may be configured in combination with the bracing rod 150, such as a flexible bracing rod, and wire 170 to allow the user 210 to move the user's head in a downward direction while still being supported by the head and neck support device 110. In one embodiment, the wire tension controller may be configured to be optionally and dynamically controlled by the user 210 at the user's hip, user's waist, user's torso, user's shoulder, users' head. In another embodiment, the wire tension controller may be configured to be optionally controlled by the user 210 at the front of the user's body, on the side of the user's body, at the back of the user's body, at the top of the user's body, in the middle of the user's body, or at the bottom of the user' body. In one embodiment, the wire tension controller may be configured to be optionally controlled by the user 210 at a single location, or at multiple locations, such as by a wire tensions control on each hip. In one embodiment, the wire tension controller may be optionally configured as a mechanical winding, a spring, ratchet, or an electronic mechanism. In another embodiment, the wire tension controller may be configured to be optionally controlled dynamically or statically by the user 210 before use, during use, or after use. The wire tension controller, my however be configured in any suitable manner to allow the user 210 to adjust, control, tighten, loosen, or maintain the tension of the wire 170 in order to increase, decrease, or maintain the level of support the neck and head support device 100 provides to the head and neck of the user 210.

In another application, the head and neck support device 100 may be configured with a quick release connector 250. In one embodiment, the quick release connector 250, may be configured as coupled to or integrated with the rail 240 and designed to retain the wire 170. In one embodiment, the quick release connector 250, may be configured as coupled to or integrated with the wire 170 and interface with the rail 240. In another embodiment, the quick release connector 250, may be configured as coupled to or integrated with the rail 240 and designed to interface with the headpiece 160. In another embodiment, the quick release connector 250, may be configured as coupled to or integrated with the wire 170 and designed to interface with the bracing rod 150. In one embodiment, the quick release connector 250, may be configured as a hook, a clip, a button, a snap, a carabiner, or another suitable method for quickly detaching the wire 170 from the rail 240. The quick release connector 250, may however be configured in any suitable manner that allows the user 210 to quickly and easily detach the headpiece 160 from the bracing rod 150 or other components of the neck and back support device 100 without the need for removing the headpiece 160 from the user's head.

Figure 6:
FIG. 6 depicts a general process diagram of a non-limiting embodiment of a head and neck support device.
Figure 6:

The head and neck support device 100 according to various aspects of an embodiment of the invention provides a method for supporting a user's head and neck using a user-wearable neck and head support device by securing a vest around a portion of a torso of a user 610; securing a headpiece around at least a portion of the user's head 620, and adjusting a tension of a wire coupled to a bracing rod coupled to a rear of the vest to apply a force pulling away from a posterior of the user's head where the wire is further slidably and detachably coupled to a rail coupled to the headpiece 630 as shown in FIG. 6.

In one embodiment, the head and neck support device 100 provides for a method for supporting a user's head and neck where the vest 110 further comprises an adjustable strap 120 and a back plate 140 coupled to the adjustable strap 120. In one embodiment, the head and neck support device 100 provides for a method for supporting a user's head and neck where the vest further comprises a hip strap 130. In another embodiment, the head and neck support device 100 provides for a method for supporting a user's head and neck where the bracket 230 is coupled to the back plate 140 and the bracing rod 150.

In one embodiment, the head and neck support device 100 provides for a method for supporting a user's head and neck using where the bracing rod 150 may be comprised of a flexible material. In one embodiment, the head and neck support device 100 provides for a method for supporting a user's head and neck using the anchor plate 220 that is coupled to the back plate 140 and the bracing rod 150. In one embodiment, the head and neck support device 100 provides for a method for supporting a user's head and neck where the bracing rod 150 is configured as a telescopic bracing rod.

In one embodiment, the head and neck support device 100 provides for a method for supporting a user's head and neck by the head and neck support device 100 configured to provide adjustment of the tension of the wire 170 by adjusting a wire tension controller within at least one of the vest 110 and the hip strap 130. In another embodiment, the head and neck support device 100 provides for a method for supporting a user's head and neck by using a wire quick-release connector 250 coupled to the wire 170. In another embodiment, the head and neck support device 100 provides for a method for supporting a user's head and neck where a diameter of the headpiece 160 is adjustable.

This disclosure, its aspects and implementations, are not limited to the specific components or assembly procedures disclosed herein. Many additional components and assembly procedures known in the art consistent with the intended head and neck support device and/or assembly procedures for head and neck support devices will become apparent for use with implementations of the head and neck support devices of this disclosure. Accordingly, for example, although particular implementations of head and neck support devices are disclosed, such head and neck support devices and implementing components may comprise any shape, size, style, type, model, version, measurement, concentration, material, quantity, and/or the like as is known in the art for such head and neck support devices and implementing components, consistent with the intended operation of head and neck support devices.

It will be understood that implementations are not limited to the specific components disclosed herein, as virtually any components consistent with the intended operation of a method and/or system for a head and neck support may be used. Accordingly, for example, although head and neck support devices may be disclosed, such components may comprise any shape, size, style, type, model, version, class, grade, measurement, concentration, material, weight, quantity, and/or the like consistent with the intended operation of a method and/or system implementation for supporting the head and neck of a wearer may be used. In places where the description above refers to particular implementations of head and neck supports, it should be readily apparent that a number of modifications may be made without departing from the spirit thereof and that these implementations may be applied to any suitable implementation of a head and neck support.

In places where the description above refers to particular implementations of systems and methods for a head and neck support device, it should be readily apparent that a number of modifications may be made without departing from the spirit thereof and that these implementations may be applied to other to systems and methods for a head and neck support device.

I claim:

1. A user-wearable neck and head support device, comprising:
   a vest;
   a bracing rod, coupled to a rear of the vest;
   a headpiece configured to seat around at least a portion of a user's head, the headpiece coupled to the bracing rod and further comprising a rail, wherein the rail is positioned proximal a rear of the user's head; and
   a wire coupled to the bracing rod and slidably and detachably coupled to the rail.

2. The user-wearable neck and head support device of claim 1, wherein the vest further comprises an adjustable strap and a back plate coupled to the adjustable strap.

3. The user-wearable neck and head support device of claim 1, wherein the vest further comprises a hip strap.

4. The user-wearable neck and head support device of claim 2, further comprising a bracket coupled to the back plate and the bracing rod.

5. The user-wearable neck and head support device of claim 1, wherein the bracing rod is comprised of a flexible material.

6. The user-wearable neck and head support device of claim 2, further comprising an anchor plate coupled to the back plate and the bracing rod.

7. The user-wearable neck and head support device of claim 1, wherein the bracing rod is telescopic.

8. The user-wearable neck and head support device of claim 3, further comprising a wire tension controller within at least one of the vest and the hip strap.

9. The user-wearable neck and head support device of claim 1, further comprising a wire quick-release connector coupled to the wire.

10. The user-wearable neck and head support device of claim 1, wherein a diameter of the headpiece is adjustable.

11. A method for supporting a user's head and neck using a user-wearable neck and head support device, the method comprising:
   securing a vest around a portion of a torso of a user;
   securing a headpiece around at least a portion of the user's head;
   adjusting a tension of a wire coupled to a bracing rod coupled to a rear of the vest to apply a force pulling away from a posterior of the user's head, the wire further slidably and detachably coupled to a rail coupled to the headpiece.

12. The method of claim 11, wherein the vest further comprises an adjustable strap and a back plate coupled to the adjustable strap.

13. The method of claim 11, wherein the vest further comprises a hip strap.

14. The method of claim 12, wherein a bracket is coupled to the back plate and the bracing rod.

15. The method of claim 11, wherein the bracing rod is comprised of a flexible material.

16. The method of claim 12, wherein an anchor plate is coupled to the back plate and the bracing rod.

17. The method of claim 11, wherein the bracing rod is telescopic.

18. The method of claim 13, wherein adjusting the tension of the wire comprises adjusting a wire tension controller within at least one of the vest and the hip strap.

19. The method of claim 11, wherein a wire quick-release connector is coupled to the wire.

20. The method of claim 11, wherein a diameter of the headpiece is adjustable.

* * * * *